(12) United States Patent
Rodriguez et al.

(10) Patent No.: US 11,801,150 B2
(45) Date of Patent: *Oct. 31, 2023

(54) GRAFT PREPARATION STATION FOR REPAIRING BONE DEFECTS

(71) Applicant: Arthrex, Inc., Naples, FL (US)

(72) Inventors: Alexander Emmanuel Rodriguez, Weston, FL (US); John David Paterson, Naples, FL (US); James Tyler Clevett, Bonita Springs, FL (US)

(73) Assignee: Arthrex, Inc., Naples, FL (US)

( * ) Notice: Subject to any disclaimer, the term of this patent is extended or adjusted under 35 U.S.C. 154(b) by 117 days.

This patent is subject to a terminal disclaimer.

(21) Appl. No.: 17/567,212

(22) Filed: Jan. 3, 2022

(65) Prior Publication Data

US 2022/0117758 A1 Apr. 21, 2022

Related U.S. Application Data

(63) Continuation of application No. 16/507,440, filed on Jul. 10, 2019, now Pat. No. 11,213,406.

(51) Int. Cl.
*A61F 2/46* (2006.01)
*A61F 2/28* (2006.01)

(52) U.S. Cl.
CPC .... *A61F 2/4644* (2013.01); *A61F 2002/2835* (2013.01); *A61F 2310/00359* (2013.01)

(58) Field of Classification Search
CPC ........ A61F 2/46; A61F 2/4644; A61F 2/4657; A61F 2002/4649; A61F 2002/4658
See application file for complete search history.

(56) References Cited

U.S. PATENT DOCUMENTS

| | | | |
|---|---|---|---|
| 4,315,494 A | 2/1982 | DiPlacido | |
| 5,540,692 A * | 7/1996 | Tidwell | A61B 17/15 606/86 R |
| 6,442,814 B1 * | 9/2002 | Landry | B23Q 1/621 409/172 |
| 6,458,144 B1 * | 10/2002 | Morris | B23C 5/1054 606/179 |
| 6,557,226 B1 * | 5/2003 | Landry | B23Q 1/621 408/23 |
| 6,676,662 B1 * | 1/2004 | Bagga | A61B 17/15 606/87 |
| 6,775,917 B1 | 8/2004 | Campbell | |

(Continued)

FOREIGN PATENT DOCUMENTS

| | | |
|---|---|---|
| DE | 102013221060 | 4/2015 |
| EP | 1444956 | 8/2004 |

OTHER PUBLICATIONS

Walch, G., Badet, R., Boulahia, A., and Khoury, A. (1999). Morphologic study of the glenoid in primary glenohumeral osteoarthritis. The Journal of Arthroplasty. vol. 14(6). 1999. pp. 756-760.

(Continued)

*Primary Examiner* — Eric S Gibson
(74) *Attorney, Agent, or Firm* — Carlson, Gaskey & Olds, P.C.

(57) ABSTRACT

This disclosure relates to a graft preparation station and methods for repairing bone defects. The station described herein may be utilized for dimensioning a graft prior to positioning the shaped graft at a surgical site.

20 Claims, 13 Drawing Sheets

(56) References Cited

U.S. PATENT DOCUMENTS

| | | | | |
|---|---|---|---|---|
| 6,962,592 B2* | 11/2005 | Gatturna | ............... | A61F 2/4644 606/184 |
| 7,699,851 B2 | 4/2010 | Dalton | | |
| 7,722,608 B2* | 5/2010 | Steiner | ................. | A61F 2/4644 606/86 R |
| 7,780,668 B2* | 8/2010 | Steiner | .................. | B25B 1/103 269/87 |
| 7,802,503 B2* | 9/2010 | Couvillion | ............... | B26D 7/02 83/762 |
| 7,879,105 B2 | 2/2011 | Schmiedling et al. | | |
| 7,955,336 B2* | 6/2011 | Gil | ........................ | A61F 2/4644 606/79 |
| 8,030,719 B2 | 10/2011 | Gunther | | |
| 8,127,646 B2* | 3/2012 | Couvillion | ............... | B26D 7/02 83/34 |
| 8,317,793 B2* | 11/2012 | Gil | ........................ | A61F 2/4644 606/79 |
| 8,322,256 B2* | 12/2012 | Vandewalle | .......... | A61F 2/4644 82/101 |
| 8,439,921 B2* | 5/2013 | Jamali | ................ | A61B 17/1668 606/86 R |
| 8,617,219 B2 | 12/2013 | Oren et al. | | |
| 9,700,438 B2* | 7/2017 | Kehres | .................... | B25B 5/163 |
| 9,918,769 B2* | 3/2018 | Provencher | ........... | A61F 2/4644 |
| 10,034,778 B2* | 7/2018 | Bosworth | ............. | A61F 2/3872 |
| 11,213,406 B2* | 1/2022 | Rodriguez | ............ | A61F 2/4644 |
| 2004/0049198 A1* | 3/2004 | Gatturna | ............... | A61F 2/4644 606/79 |
| 2004/0220578 A1* | 11/2004 | Bagga | .................. | A61F 2/4644 606/87 |
| 2008/0011137 A1* | 1/2008 | Couvillion | ............... | B26D 7/02 83/78 |
| 2008/0215052 A1* | 9/2008 | Steiner | .................. | A61F 2/4644 606/53 |
| 2008/0255562 A1* | 10/2008 | Gil | ........................ | A61F 2/4644 606/79 |
| 2008/0255623 A1* | 10/2008 | Steiner | ...................... | B25B 3/00 606/86 R |
| 2009/0209963 A1* | 8/2009 | Jamali | ...................... | A61F 2/34 606/89 |
| 2009/0234452 A1* | 9/2009 | Steiner | .................. | A61F 2/4644 623/14.12 |
| 2010/0268238 A1 | 10/2010 | Sikora et al. | | |
| 2012/0253350 A1* | 10/2012 | Anthony | ................. | A61B 17/14 606/87 |
| 2013/0096680 A1* | 4/2013 | Ribeiro | ................. | A61F 2/3872 606/88 |
| 2013/0238099 A1 | 9/2013 | Hardy et al. | | |
| 2014/0025173 A1 | 1/2014 | Cardon et al. | | |
| 2015/0297361 A1* | 10/2015 | Kehres | .................... | B25B 5/102 83/13 |
| 2016/0270933 A1* | 9/2016 | Bosworth | ............. | A61F 2/3872 |
| 2016/0345987 A1 | 12/2016 | Guilloux et al. | | |
| 2017/0056085 A1* | 3/2017 | Provencher | ........ | A61B 17/8863 |
| 2017/0273795 A1* | 9/2017 | Neichel | ................. | A61F 2/4644 |
| 2021/0007863 A1* | 1/2021 | Rodriguez | ............ | A61F 2/4644 |
| 2022/0117758 A1* | 4/2022 | Rodriguez | ............ | A61F 2/4644 |

OTHER PUBLICATIONS

International Search Report & Written Opinion for International Application No. PCT/ US2020/041347 completed Oct. 8, 2020.
International Preliminary Report on Patentability for International Application No. PCT/US2020/041347 dated Jan. 20, 2022.

\* cited by examiner

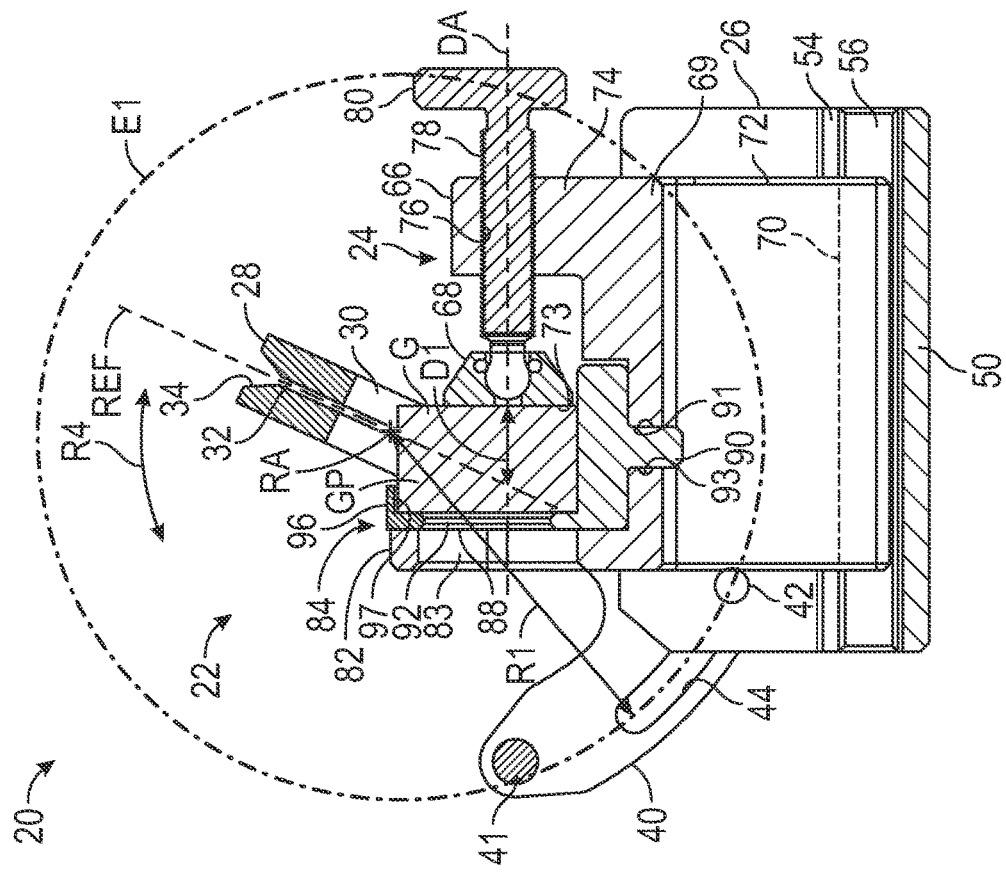

GRAFT PREPARATION STATION FOR REPAIRING BONE DEFECTS

CROSS-REFERENCE TO RELATED APPLICATIONS

This application is a continuation of U.S. application Ser. No. 16/507,440, filed Jul. 10, 2019.

BACKGROUND

This disclosure relates to surgical devices and methods for repairing bone defects.

Many bones of the human musculoskeletal system include articular surfaces. The articular surfaces articulate relative to other bones to facilitate different types and degrees of joint movement. The articular surfaces can erode (i.e., experience bone loss) over time due to repeated use or wear or can fracture as a result of a traumatic impact. These types of bone defects can cause joint instability and pain.

Bone deficiencies may occur along the articular surfaces of the glenoid bone. Some techniques utilize a bone graft to a fill defect in the glenoid bone.

SUMMARY

This disclosure relates to surgical devices and methods. The surgical device may be used during methods for repairing bone defects. The surgical devices described herein may be utilized to dimension a graft relative to a predefined thickness and/or angle based on a geometry of the bone defect.

A graft preparation station for dimensioning a bone graft according to an embodiment of the present disclosure includes, inter alia, a base assembly including a support body and a base guide pivotably mounted to the support body to bound a passageway, the base guide defining a cutting slot extending outwardly from the passageway, and a cart assembly including a cart body and a mounting plate dimensioned to mount a bone graft, the cart body translatable relative to a drive axis intersecting the passageway to set a distance between the cutting slot and the mounting plate.

A graft preparation station for dimensioning a bone graft according to an embodiment of the present disclosure includes, inter alia, a base assembly including a support body and a base guide pivotably mounted to the support body, the base guide defining a cutting slot extending along a reference plane, and a cart assembly including a mounting plate and a raise plate both secured to a cart body, the mounting plate moveable along a drive axis relative to the cart body to secure a bone graft between the mounting plate and the raise plate, and the cart body slidably received in the support body such that the reference plane intersects the drive axis at a position between the raise plate and the mounting plate.

A method of preparing a bone graft according to an embodiment of the present disclosure includes, inter alia, positioning a bone graft between a mounting plate of a cart assembly and a raise plate secured to the cart assembly, translating the cart assembly along a drive axis relative to a base assembly, the base assembly including a base guide defining a cutting slot along a reference plane, and the drive axis intersecting the reference plane and the mounting plate, pivoting the base guide to adjust an angle of the reference plane relative to the drive axis, and moving a cutting tool through the cutting slot to cut the bone graft at a position between the mounting plate and the raise plate.

BRIEF DESCRIPTION OF THE DRAWINGS

FIG. 4 illustrates a side view of the station of FIG. 1.

FIG. 5 illustrates a sectional view of the station of FIG. 4.

DETAILED DESCRIPTION

Figure 1:
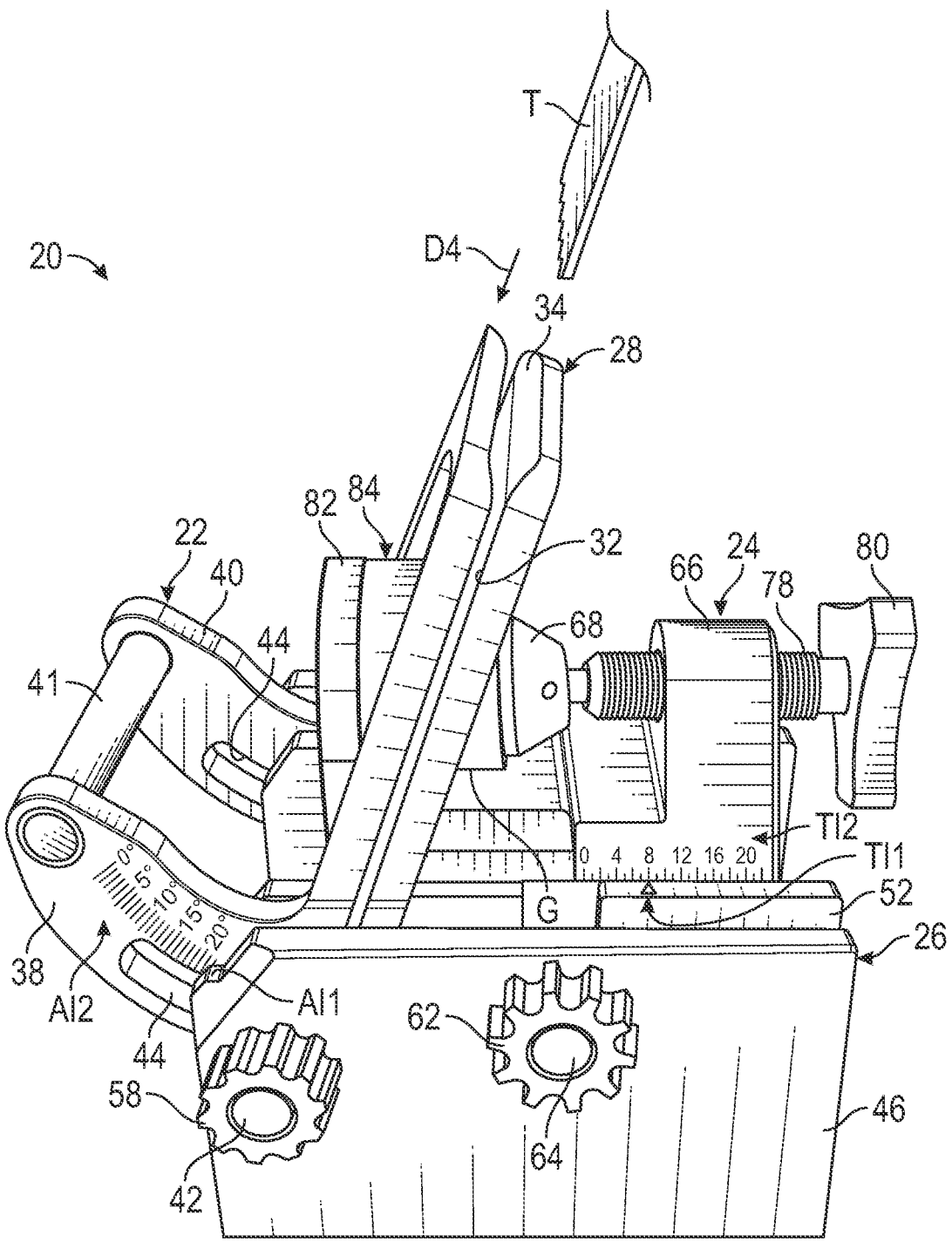
FIG. 1 illustrates a perspective view of a graft preparation station including a base assembly and a cart assembly for preparing a graft.

This disclosure relates to surgical devices and methods for repairing bone defects. The devices described herein may be capable of dimensioning or otherwise preparing a bone graft that is positioned at a surgical site to fill a bone void. The graft can be shaped to a specified angle and/or thickness corresponding to a geometry of the bone void.

A graft preparation station for dimensioning a bone graft according to an exemplary aspect of the present disclosure includes, inter alia, a base assembly including a support body and a base guide pivotably mounted to the support body to bound a passageway, the base guide defining a cutting slot extending outwardly from the passageway, and a cart assembly including a cart body and a mounting plate dimensioned to mount a bone graft, the cart body translatable relative to a drive axis intersecting the passageway to set a distance between the cutting slot and the mounting plate.

In a further embodiment, the base guide includes first and second arm portions extending from a guide body, the guide body is dimensioned to bound the passageway, and the first and second arm portions are pivotably mounted to the support body.

In a further embodiment, each of the first and second arm portions defines an arcuate slot dimensioned to receive a plurality of guide pins fixedly attached to the support body.

In a further embodiment, the support body includes first and second sidewalls extending from a base to bound the passageway, and the first and second sidewalls define respective support channels dimensioned to receive the first and second arm portions.

In a further embodiment, each guide pin of the plurality of guide pins spans between opposed walls of a respective one of the support channels.

In a further embodiment, the cutting slot is defined along a reference plane extending through the passageway. A control knob is translatable along one of plurality of guide pins to set a cutting angle of the reference plane relative to a rotational axis of the base guide in response to the control knob abutting against the first arm portion.

In a further embodiment, the cart body includes first and second guide rails extending outwardly from opposed sidewalls of the cart body, and the support body defines a pair of guide channels dimensioned to slidably receive the first and second guide rails.

In a further embodiment, a raise plate is releasably secured to the cart body, the raise plate defining a plate opening dimensioned to receive the bone graft along the drive axis.

In a further embodiment, the mounting plate is moveable along the drive axis to compress the bone graft between the raise plate and the mounting plate.

In a further embodiment, the cutting slot is defined along a reference plane extending through the passageway, the cart assembly includes a support flange extending outwardly from the cart body, and the support flange defines a flange opening dimensioned such that the plate opening is arranged between the flange opening and the mounting plate relative to the drive axis.

In a further embodiment, the cart body includes first and second guide rails extending outwardly from opposed sidewalls of the cart body, the support body defines an opposed pair of guide channels dimensioned to slidably receive the first and second guide rails, and the drive axis intersects the reference plane in response to inserting the first and second guide rails in the pair of guide channels.

In a further embodiment, the base guide includes first and second arm portions extending from a guide body, and the guide body is dimensioned to bound the passageway, each of the first and second arm portions defines an arcuate slot dimensioned to receive one or more guide pins fixedly attached to the support body such that the first and second arm portions are pivotably mounted to the support body, and each arcuate slot is dimensioned such that a rotational axis of the base guide is spaced apart from the first and second arm portions.

A graft preparation station for dimensioning a bone graft according to an exemplary aspect of the present disclosure includes, inter alia, a base assembly including a support body and a base guide pivotably mounted to the support body, the base guide defining a cutting slot extending along a reference plane, and a cart assembly including a mounting plate and a raise plate both secured to a cart body, the mounting plate moveable along a drive axis relative to the cart body to secure a bone graft between the mounting plate and the raise plate, and the cart body slidably received in the support body such that the reference plane intersects the drive axis at a position between the raise plate and the mounting plate.

In a further embodiment, a plurality of guide pins are fixedly attached to the support body, and the plurality of guide pins are received in arcuate slots defined in first and second arm portions of the base guide to secure the base guide to the support body.

In a further embodiment, the arcuate slots are dimensioned such that a rotational axis of the base guide is spaced apart from the arcuate slots, the rotational axis defined along the reference plane.

[own] A method of preparing a bone graft according to an exemplary aspect of the present disclosure includes, inter alia, positioning a bone graft between a mounting plate of a cart assembly and a raise plate secured to the cart assembly, translating the cart assembly along a drive axis relative to a base assembly, the base assembly including a base guide defining a cutting slot along a reference plane, and the drive axis intersecting the reference plane and the mounting plate, pivoting the base guide to adjust an angle of the reference plane relative to the drive axis, and moving a cutting tool through the cutting slot to cut the bone graft at a position between the mounting plate and the raise plate.

In a further embodiment, the positioning step includes compressing the bone graft between the mounting plate and the raise plate.

In a further embodiment, the method includes selecting the raise plate from a plurality of raise plates, each of plurality of raise plates defined with respect to a different graft diameter, and mounting the raise plate to the cart assembly such that the plate opening extends along the drive axis.

In a further embodiment, the pivoting step includes moving the base guide relative to a plurality of guide pins fixedly attached to a support body of the base assembly, the plurality of guide pins received in arcuate slots defined in the base guide, and the arcuate slots are spaced apart from a rotational axis of the base guide.

In a further embodiment, the translating step includes sliding a pair of guide rails of the cart assembly relative to an opposed pair of guide channels defined by the support body such that the drive axis intersects the reference plane.

FIGS. 1-5 illustrate an exemplary graft preparation station 20 that can be utilized for shaping or otherwise preparing a graft. The station 20 can be utilized for dimensioning or shaping a graft G secured to the station 20. The graft G may include various sizes and shapes and may be sized and shaped to substantially conform to the geometry of the bone. The harvested graft G can have a generally cylindrical or rectangular geometry, for example. Although the disclosure primarily refers to the graft G being a bone graft, such as autologous bone harvested from a humeral head, it should be appreciate that the graft G may additionally be formed of various materials. The graft G could be any type of graft formed from any type of material, including but not limited to, autograft bone, allograft bone, metals, plastics, synthetic materials, or any combination of these materials. The station 20 may be used to perform a variety of surgical procedures such as a shoulder reconstruction in which a shaped portion of the graft G is utilized to fill a bone defect in the glenoid of a patient.

Figure 2:
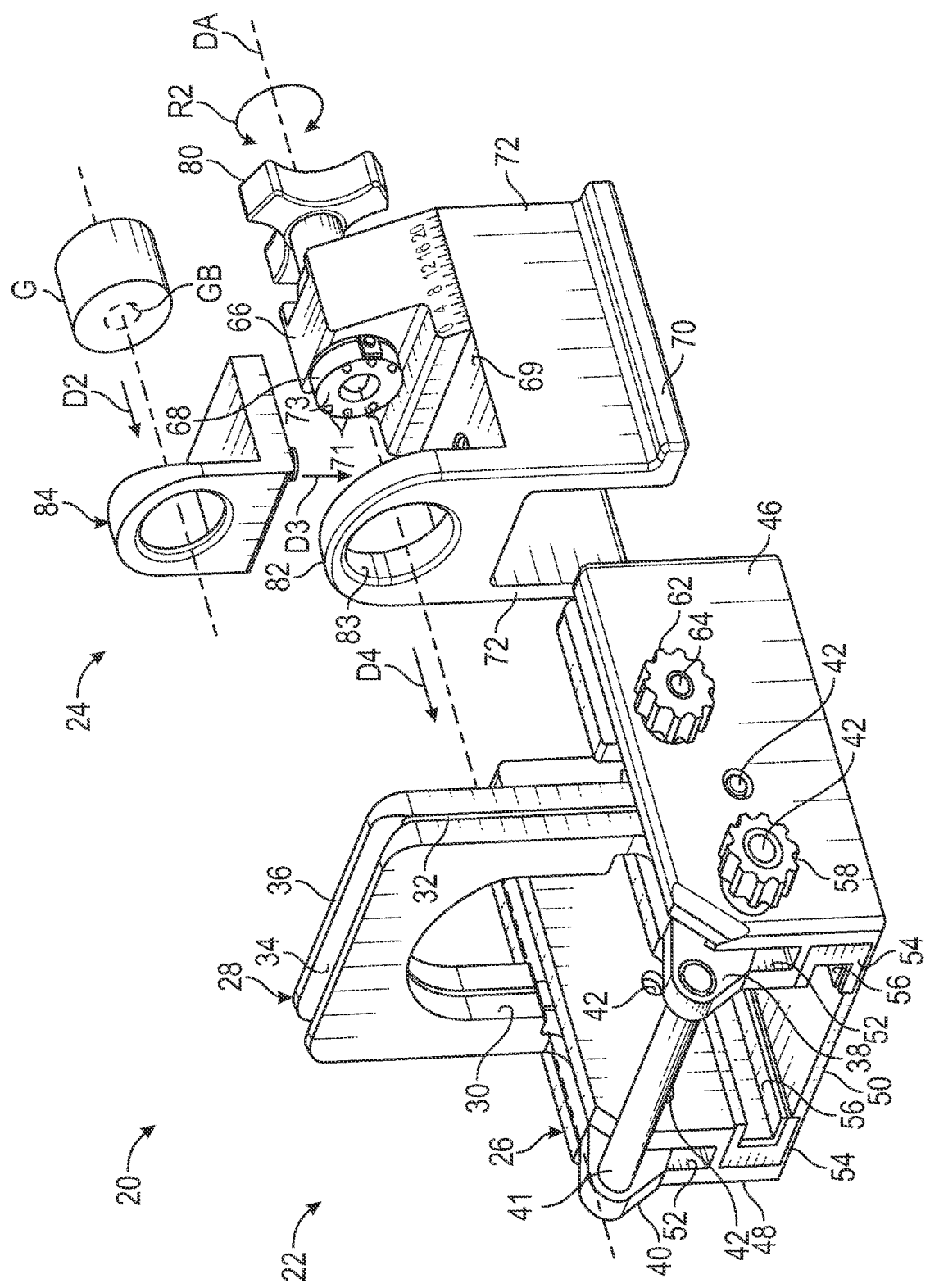
FIG. 2 illustrates a perspective view of the station of FIG. 1 in a partially unassembled position.
Figure 3:
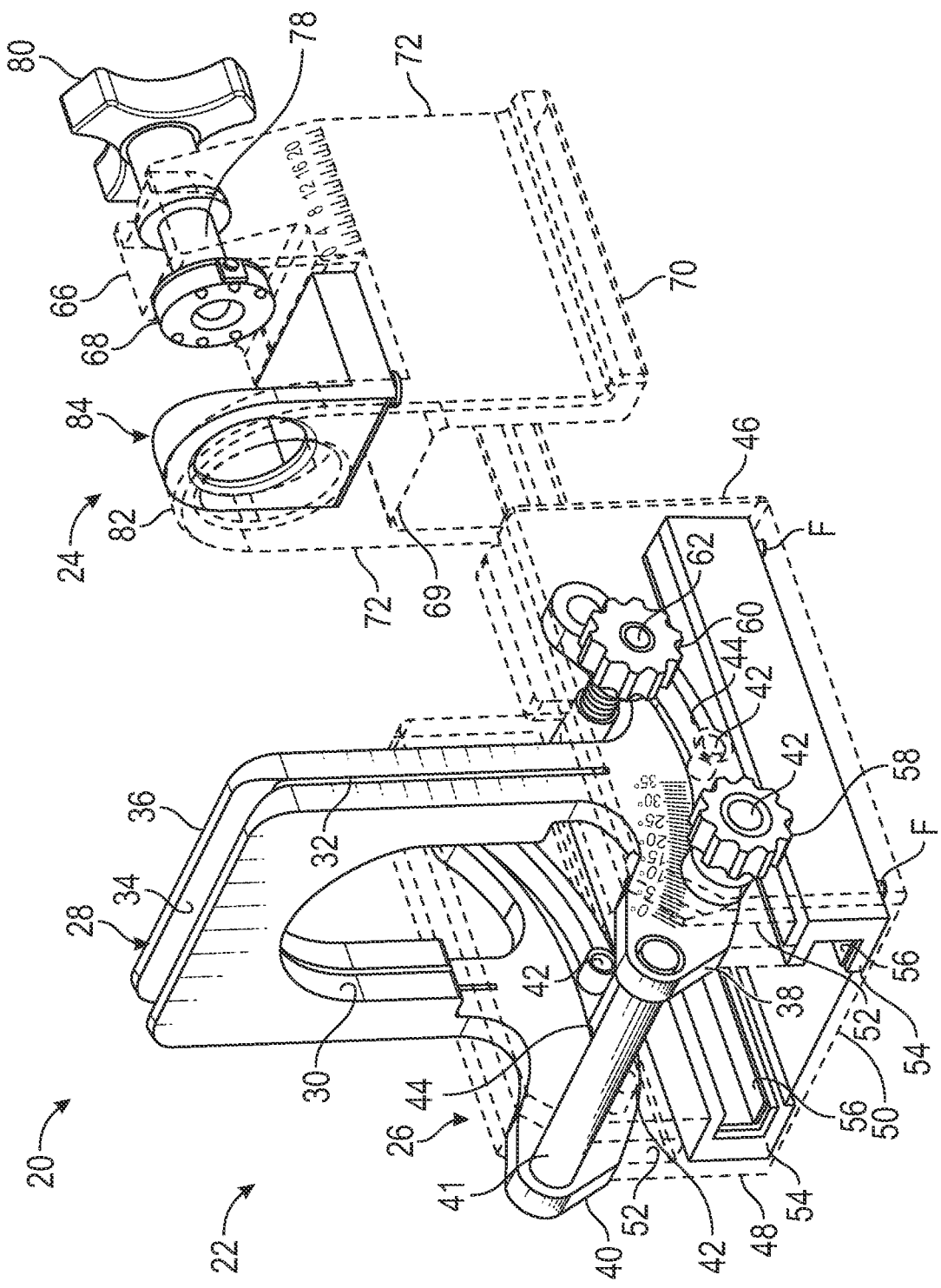
FIG. 3 illustrates a perspective view of the station of FIG. 3 with portions shown in phantom.

Referring to FIGS. 1-3, the station 20 includes a base assembly 22 releasably secured to a cart assembly 24. The cart assembly 24 is at least partially received in the base assembly 22 to position the graft G relative to the base assembly 22, as illustrated in FIGS. 1 and 4-5. Of course, an opposite configuration is also contemplated in which the base assembly 22 is at least partially received in the cart assembly 24.

The base assembly 22 includes a support body 26 and a base guide 28. The base guide 28 is pivotably mounted to the support body 26 to establish a passageway 30 dimensioned to at least partially receive the cart assembly 24, as illustrated in FIGS. 1 and 5. Walls of the support body 26 and base guide 28 are dimensioned to bound a perimeter of the passageway 30 in an installed position. The base guide 28 establishes an archway over the graft G, as illustrated by FIGS. 1 and 4-5.

The base guide 28 defines a cutting slot 32 extending outwardly from the passageway 30. The cutting slot 32 is defined along a reference plane REF extending through the passageway 30 (REF shown in dashed lines in FIGS. 4-5). The cutting slot 32 is dimensioned to receive a cutting tool or instrument T such as an oscillating saw having a sagittal blade (FIG. 1). A thickness of the saw blade can be less than or about 1 mm, for example. The cutting slot 32 can include a tapered groove 34 that slopes inwardly from a wall of the base guide 28. The tapered groove 34 can serve to guide the blade of the instrument T inwardly along the cutting slot 32.

The base guide 28 includes a guide body 36 that extends generally laterally between opposed first and second sidewalls 46, 48 of the support body 26. The guide body 36 has a generally U-shape geometry to bound the passageway 30, as illustrated in FIGS. 2-3. The base guide 28 includes first and second (or a pair of) arm portions 38, 40 that extend outwardly from the guide body 36. The arm portions 38, 40 are pivotably mounted to the support body 26 with a plurality of guide pins 42 (FIGS. 2-3). Each arm portion 38, 40 has a generally arcuate geometry. Other geometries of the arm portions 38, 40, such as a generally rectangular geometry.

Figure 8:
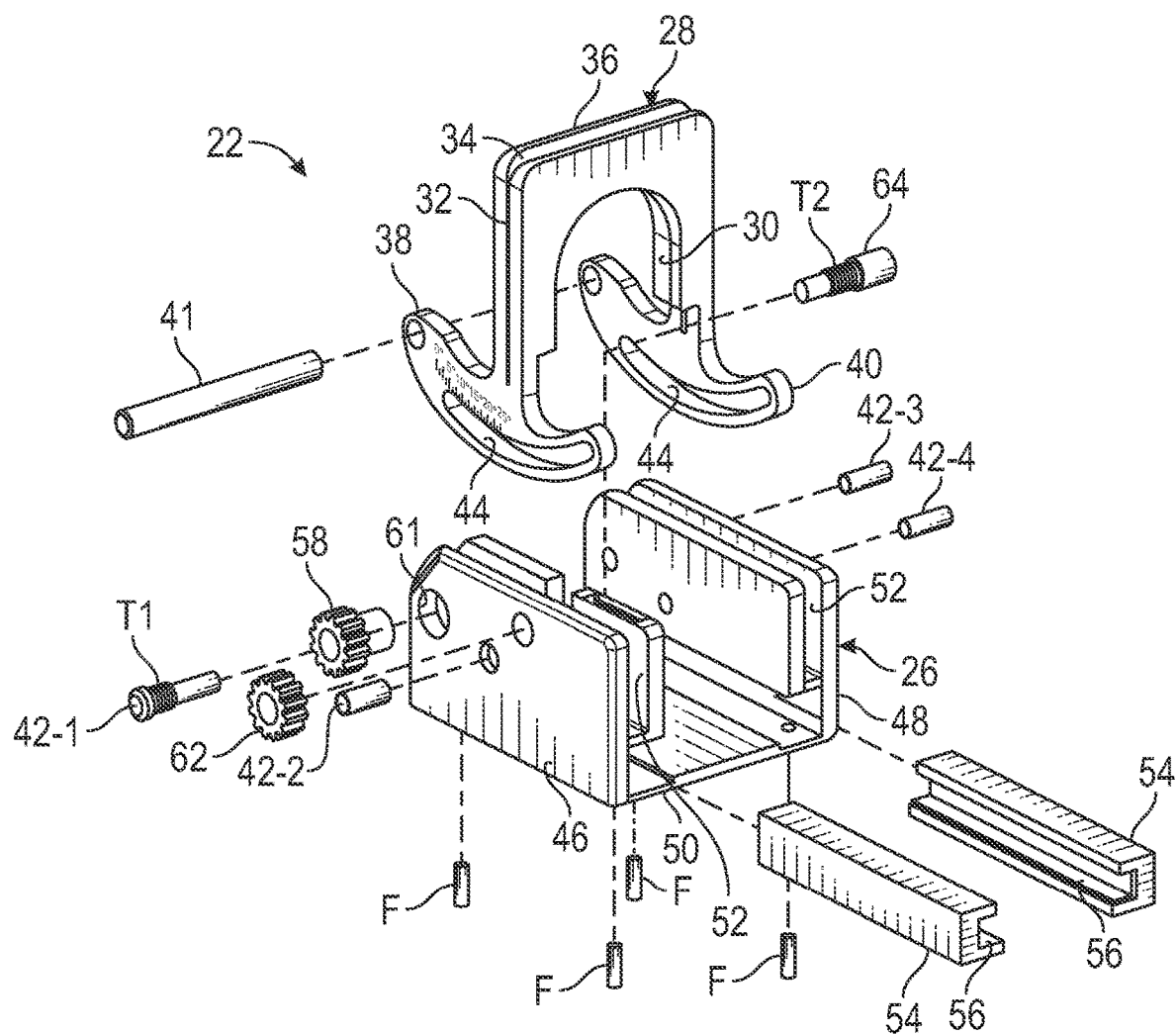
FIG. 8 illustrates an exploded view of the base assembly of FIG. 6.

Referring to FIGS. 4-5 and 8, with continued reference to FIGS. 1-3, each of the arm portions 38, 40 defines an arcuate slot 44. Each arcuate slot 44 is dimensioned to receive one or more of the guide pins 42. The guide pins 42 are fixedly attached to the support body 26 to secure the base guide 28 to the support body 26. The guide pins 42 can be welded or threadably secured to the support body 26, for example. The guide pins 42 are received in and extend through the arcuate slots 44 such that the arm portions 38, 40 are pivotably mounted to the support body 26. Pivoting the base guide 28 includes moving the base guide 28 relative to the guide pins 42. In the illustrative embodiment of FIG. 8, the base assembly 22 includes four guide pins 42 (indicated at 42-1 to 42-4). It should be appreciated that fewer or more than four guide pins 42 can be utilized.

In the illustrative embodiment of FIGS. 4-5, the guide pins 42 are mechanically attached at different positions along the support body 26 to establish a rotational axis RA defined along the reference plane REF. Each guide pin 42 is positioned along an ellipse E1 (shown in dashed lines) defined by a radius R1. The radius R1 extends from and is swept about the rotational axis RA to define the ellipse E1. Each arcuate slot 44 is dimensioned with respect to the radius R1 such that the arcuate slot 44 extends a distance along the ellipse E1. The arcuate slots 44 are dimensioned such that the rotational axis RA is spaced apart from the arcuate slots 44 and the arm portions 38, 40.

Figure 6:
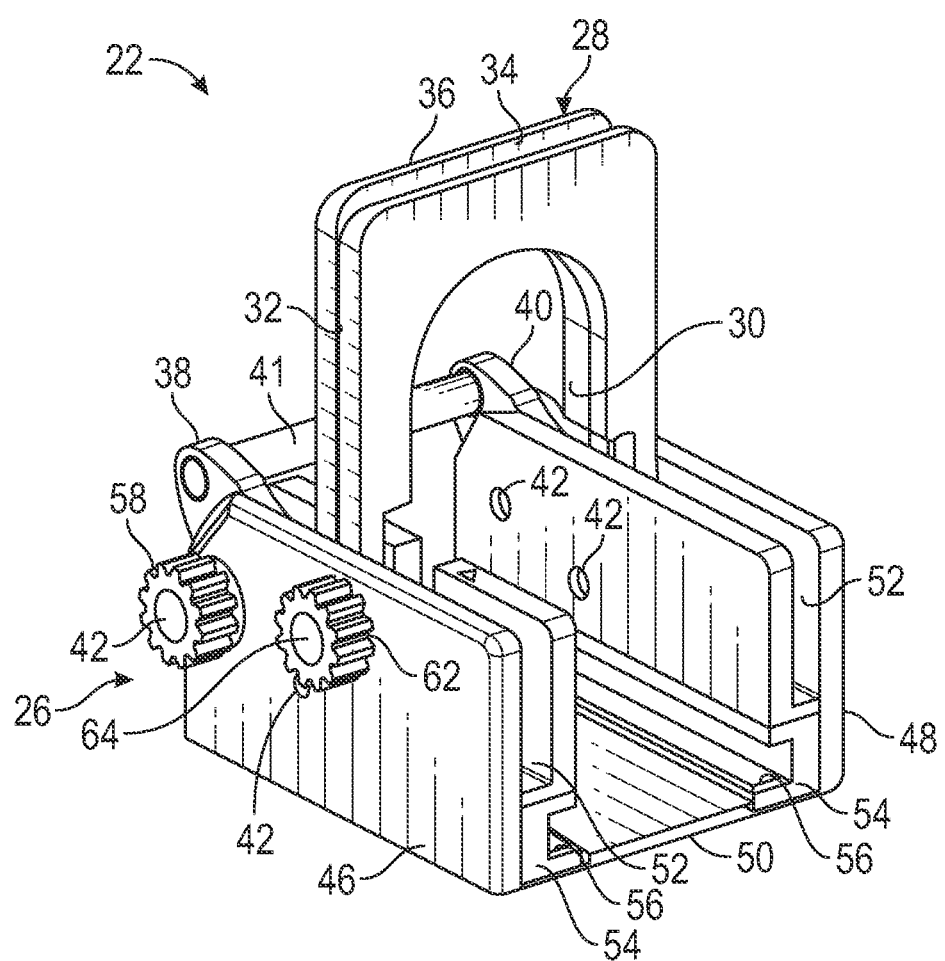
FIGS. 6 and 7 illustrate perspective views of the base assembly of FIG. 1.
Figure 7:
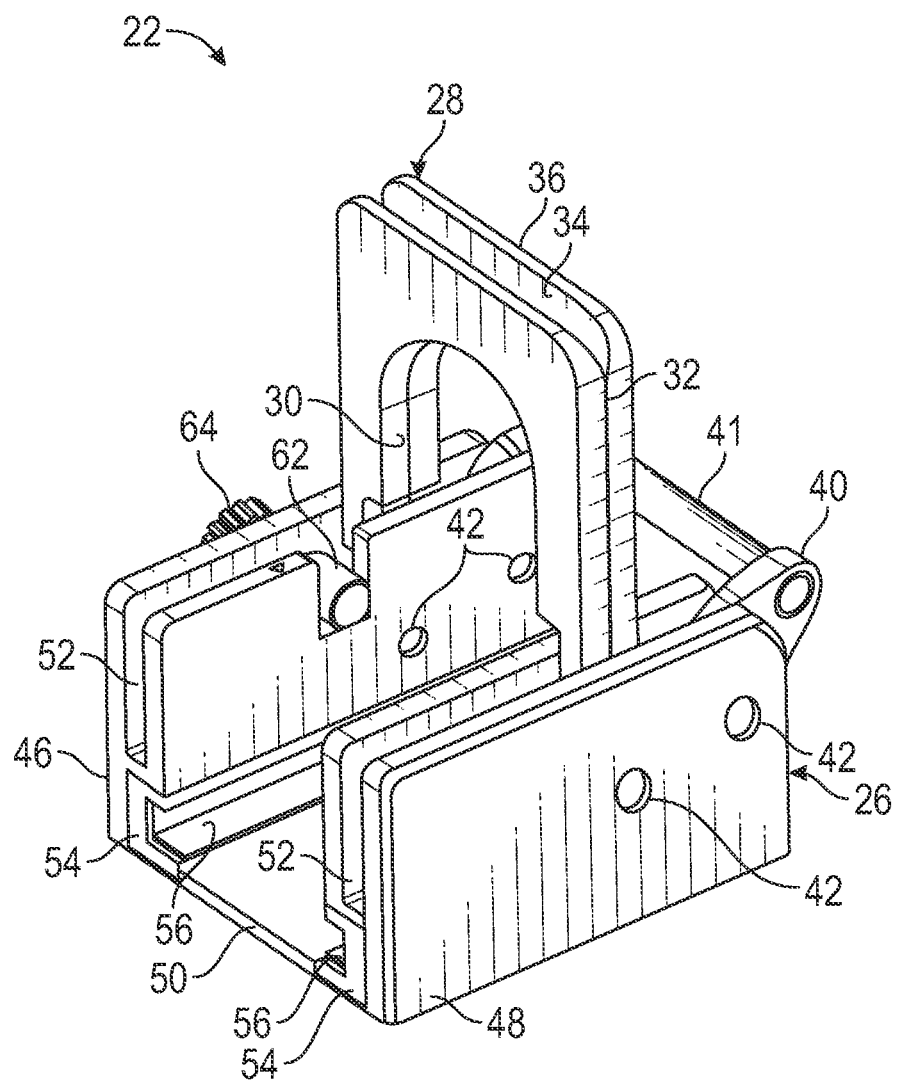

Referring to FIGS. 6-8, with continued reference to FIGS. 1-5, the base guide 28 can include a crossbar 41 spanning between and fixedly attached to ends of the arm portions 38, 40. The crossbar 41 can provide rigidity to the arm portions 38, 40 and can serve as a handle for adjusting a rotational position of the base guide 28.

The sidewalls 46, 48 extend from a base 50 to bound the passageway 30. The sidewalls 46, 48 are dimensioned to at least partially receive the cart assembly 24 in the passageway 30. The sidewalls 46, 48 respectively define a pair of support channels 52 that extend between opposed ends of the support body 26. The support channels 52 are dimensioned to receive respective ones of the arm portions 38, 40, as illustrated by FIGS. 1-3. Each guide pin 42 spans between opposed walls of a respective one of the support channels 52 (see FIGS. 3 and 6-7).

The support body 26 includes an opposed pair of guide channels 56 that cooperate with the cart assembly 24. In the illustrated example of FIGS. 2-3 and 5-8, the base assembly 22 includes a pair of track bearings 54. The track bearings 54 are mounted to respective sidewalls 46, 48 of the support body 26 to define the guide channels 56. The track bearings 54 can be mounted or secured to the base 50 utilizing one or more fasteners F (FIGS. 3 and 8). In other embodiments, the guide channels 56 are defined in a thickness of the sidewalls 46, 48 of the support body 26.

The base assembly 22 can include one or more control features to set various dimensions of the bone graft G (FIGS. 1 and 4-5). The base assembly 22 includes a first control knob 58 that is configured to set a cutting angle of the cutting slot 32 relative to the base 50. A portion of the control knob 58 is received in bore 61. The control knob 58 cooperates with threading T1 along the guide pin 42-1. The control knob 58 is configured to set a cutting angle of the reference plane REF (FIG. 4) and cutting slot 32 relative to the rotational axis RA (FIG. 4).

The control knob 58 is dimensioned such that rotation of the control knob 58 causes the control knob 58 to translate along the guide pin 42-1 and abut against the first arm portion 38 (see FIG. 3). Abutment of the control knob 58 against the first arm portion 38 opposes relative movement to set the cutting angle of the reference plane REF relative to the rotational axis RA of the base guide 28. The guide pins 42 and arcuate slots 44 define a range of cutting angles for selection by the surgeon. The range of cutting angles can include a minimum cutting angle greater than approximately 0 degrees and a maximum cutting angle equal to or less than approximately 35 degrees, for example. In embodiments, the minimum cutting angle is at least approximately 5 or 10 degrees. A surgeon can orient the base guide 28 relative to the range of cutting angles for dimensioning the bone graft G. In the illustrative embodiment of FIG. 1, the cutting angle is set at approximately 20 degrees. In the illustrative embodiment of FIGS. 4-5, the cutting angle is set at approximately 25 degrees. It should be appreciated a maximum cutting angle can be greater or lesser than 35 degrees, such as equal to or less than approximately 45 degrees. For the purposes of this disclosure, the term "approximately" means ±3% of the stated value unless otherwise stated.

The base assembly 22 can include a second control knob 62 configured to set a thickness of the bone graft G to be prepared. The control knob 62 cooperates with threading T2 (FIG. 8) along the engagement pin 64 to fixedly attach the control knob 62 to the engagement pin 64. The engagement pin 64 is dimensioned to selectively abut against the cart assembly 24 in response to rotation of the control knob 62 to oppose relative movement. The base assembly 22 and cart assembly 24 are dimensioned to establish a range of maximum thicknesses for dimensioning a thickness or width of the graft G, such as between 0 millimeters (mm) and equal to or less than approximately 25 mm. In the illustrative embodiment of FIG. 4, the thickness is set at approximately 0 mm. In the illustrative embodiment of FIG. 1, the thickness is set at approximately 8 mm.

Figure 9:
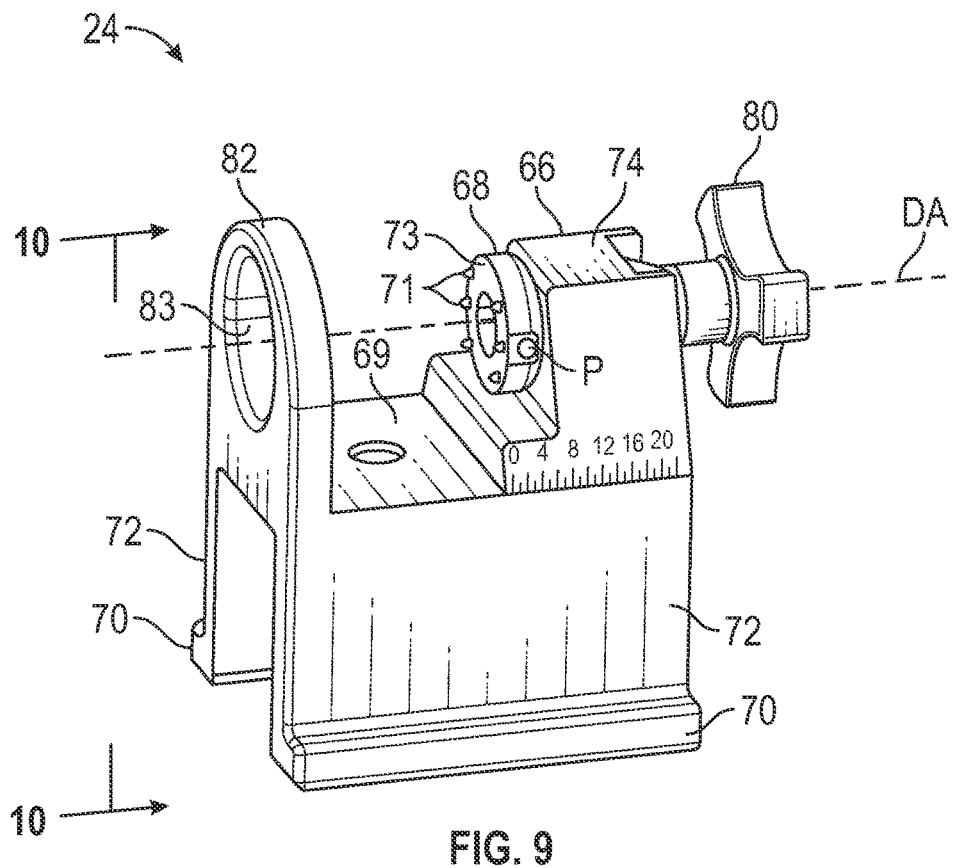
FIG. 9 illustrates a perspective view of a cart assembly.
Figure 10:
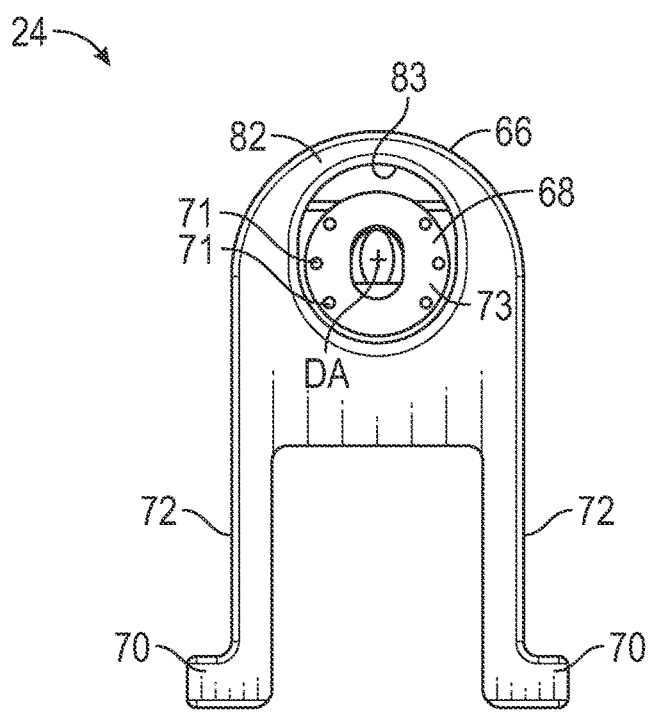
FIG. 10 illustrates a front view of the cart assembly of FIG. 9.
Figure 11:
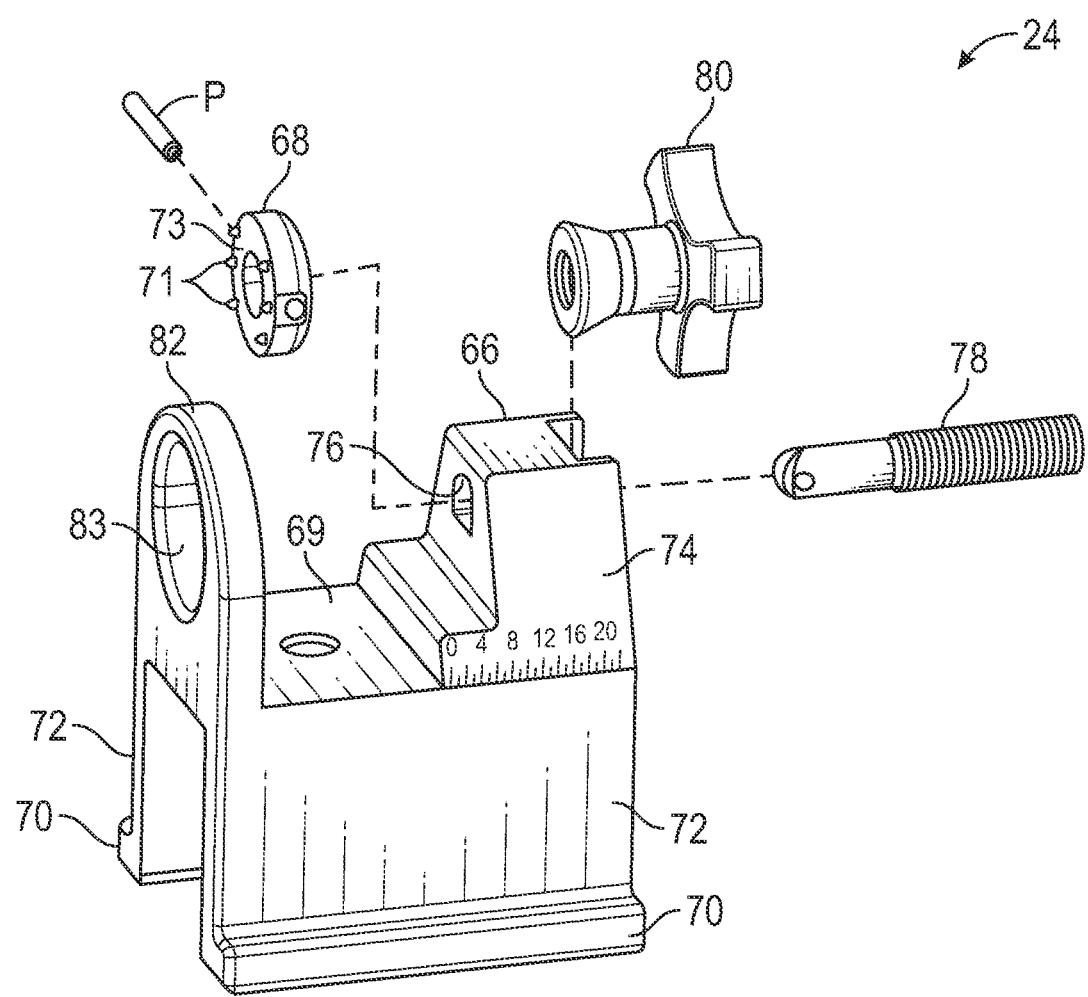
FIG. 11 illustrates an exploded view of the cart assembly of FIG. 9.

Referring to FIGS. 9-11, with continued reference to FIGS. 1-5, the cart assembly 24 is shown. The cart assembly 24 includes a cart body 66 and a tilt (or mounting) plate 68 dimensioned to mount the graft G, as illustrated in FIGS. 1 and 4-5. The cart body 66 includes a platform 69 and first and second guide rails 70 that extend outwardly from opposed sidewalls 72 of the cart body 66. The guide channels 56 are dimensioned to mate with and slidably receive the guide rails 70 (see FIG. 5).

A raised portion 74 extends outwardly from the platform 69. The raise portion 74 defines a bore 76 dimensioned to threadably receive a clamp screw 78 (FIGS. 5 and 11). An end of the tilt plate 68 can be mounted to the clamp screw 78 to establish a swivel joint. The end of the clamp screw 78 can be mechanically attached to the tilt plate 68 utilizing a fastener such as a pin P to secure the tilt plate 68 to the cart body 66, for example. The tilt plate 68 can include one or more protrusions or teeth 71 extending outwardly from a proximal face 73 to engage the graft G (see also FIG. 2).

The cart assembly 24 includes a clamp knob 80 mechanically attached to another end of the clamp screw 78. In the illustrative embodiment of FIGS. 1 and 4-5, the clamp screw 78 is integrally formed with the claim knob 80. The clamp screw 78 extends along or otherwise defines a drive axis DA. Rotation of the clamp knob 80 causes the clamp screw 78 to translate along the drive axis DA.

The cart assembly 24 includes a support flange 82 extending outwardly from the platform 69 of the cart body 66. The support flange 82 defines an access hole or flange opening 83.

As illustrated by FIG. 5, the drive axis DA intersects the reference plane REF along the passageway 30 in response to inserting the guide rails 70 in the guide channels 56. Once inserted into the support body 26, the cart body 66 is translatable relative to the drive axis DA to set a distance D1 between the cutting slot 32 along the reference plane REF and the proximal face 73 of the tilt plate 68 (see also FIG. 4). The flange opening 83 is defined along the drive axis DA.

Figure 12:
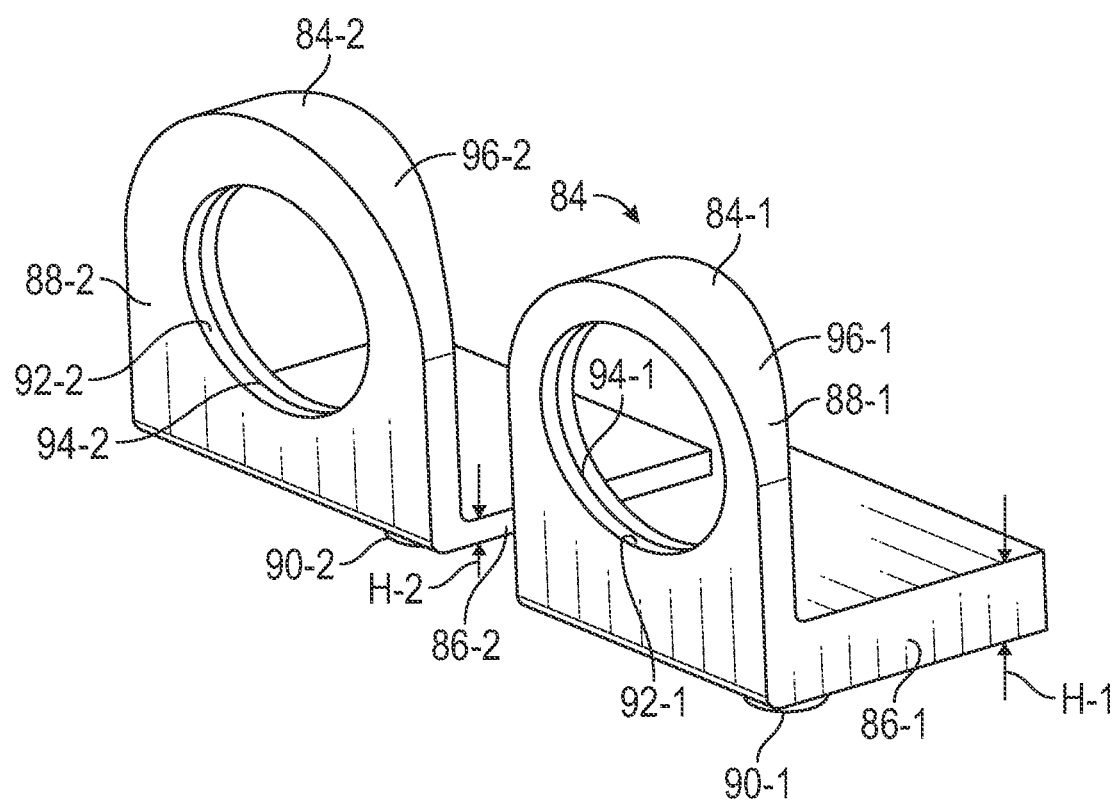
FIG. 12 illustrates an exemplary set of raise plates.

Referring to FIGS. 12-15, with continued reference to FIGS. 1-5, the station 20 includes one or more raise plates (or graft trays) 84 for carrying or otherwise supporting the graft G (two raise plates indicated at 84-1, 84-2 in FIG. 12 for illustrative purposes). The raise plate 84 can be releasably secured to the platform 69 of the cart body 66, as illustrated by FIG. 5 (see also FIGS. 1 and 4).

Figure 15:
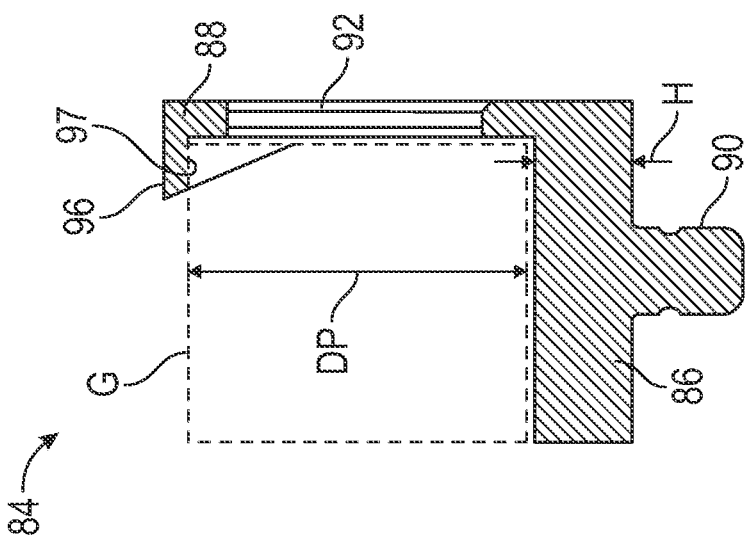
FIG. 15 illustrates a sectional view of the raise plate taken along line 15-15 of FIG. 14.
Figure 14:
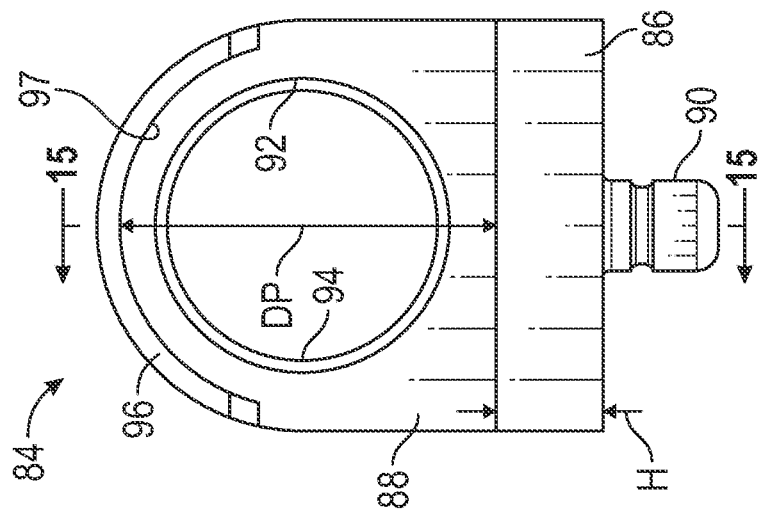
FIGS. 13 and 14 illustrate front and rear views of one of the raise plates of FIG. 12.
Figure 13:
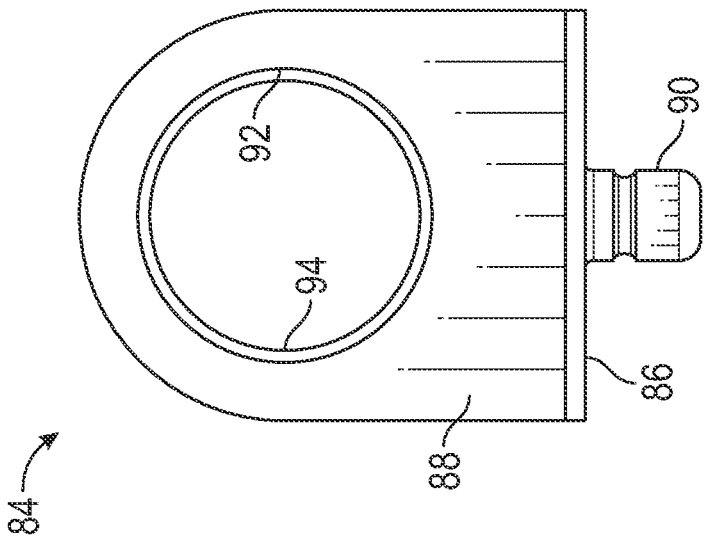

The raise plate 84 has a generally L-shaped geometry and includes a base portion 86 and a flange portion 88 extending outwardly from the base portion 86. The base portion 86 defines a height H (FIGS. 14-15). The respective bone graft G sits on the base portion 86. Each raise plate 84 can be dimensioned with respect to a different height H to accommodate bone grafts G of various sizes. In the illustrative embodiment of FIG. 12, raise plate 84-1 has a relatively greater height H-1 than a height H-2 of raise plate 84-2 to elevate the bone graft G relative to the platform 69. The height H can be defined such that a perimeter of the graft G is substantially flush with the rotational axis RA, as illustrated in FIG. 5.

An elongated peg or stem 90 extends outwardly from the base portion 86. The stem 90 is dimensioned to be inserted into an opening 91 in the platform 69 to secure the raise plate 84, as illustrated in FIG. 5. A retention feature 93 (FIG. 5) can be disposed along the opening 91 to oppose withdrawal of the stem 90. The retention feature 93 can be formed from an elastic or other deformable material, for example.

The raise plate 84 can include an arcuate flange 96 extending outwardly from the flange portion 88 to establish a graft cavity 97. The graft cavity 97 is dimensioned to at least partially receive the graft G, as illustrated in FIG. 15. The arcuate flange 96 extends along a diameter DP corresponding to a circumference of a respective graft G (shown in dashed lines in FIG. 15 for illustrative purposes) to bound the graft cavity 97. The arcuate flange 96 can be dimensioned to establish an interference fit with the graft G along the graft cavity 97. Each raise plate 84 can be dimensioned with respect to a different diameter DP to accommodate bone grafts G of various sizes. For example, raise plate 84-1 can define a diameter DP of approximately 25 mm, and raise plate 84-2 can define a diameter DP of approximately 30 to accommodate a relatively wider graft G. The arcuate flange 96 is dimensioned to at least partially surround and bound circumferential movement of the graft G in the graft cavity 97 relative to the drive axis DA, as illustrated by FIG. 5 (see also FIG. 4). The surgeon can urge the graft G toward the flange portion 88 to wedge or capture the graft G in the graft cavity 97.

The flange portion 88 defines a plate opening 92. The flange opening 83 can serve to provide access to the graft G in the graft cavity 97. In the illustrative embodiment of FIG. 5, the flange opening 83 can be dimensioned such that the plate opening 92 is arranged between the flange opening 83 and the tilt plate 68 relative to the drive axis DA. Subsequent to shaping the graft G, the surgeon may insert a finger or instrument through the flange opening 83 and plate opening 92 to move the graft G outward of the graft cavity 97.

As illustrated in FIG. 5, the tilt plate 68 is moveable along the drive axis DA relative to the cart body 66 to trap or otherwise secure the graft G between the tilt plate 68 and the flange portion 88 of the raise plate 84 (see also FIGS. 1 and 4). Once the graft G is secured to the raise plate 84, the tilt plate 68 can be moved a distance along the drive axis DA to clamp or compress the bone graft G between the tilt plate 68 and the flange portion 88. The cart body 66 is slidably received in the support body 26 such that the reference plane REF intersects the drive axis DA at a position between the flange portion 88 of the raise plate 84 and the proximal face 73 of the tilt plate 68. The drive axis DA intersects reference plane REF and the tilt plate 68.

Figure 16:
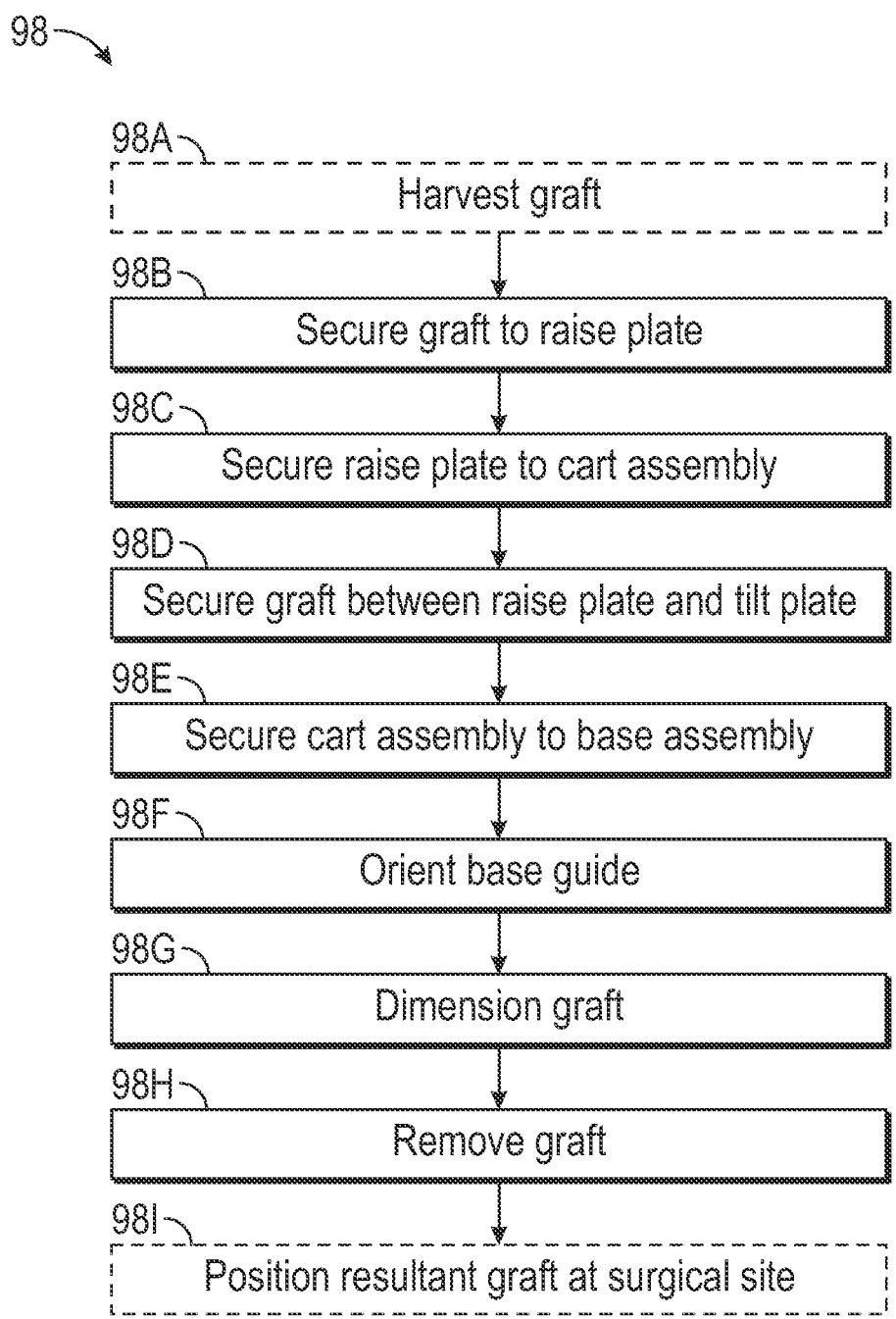
FIG. 16 illustrates an exemplary method for forming a graft.

An example method of use will now be described. Referring to FIG. 16, an exemplary method in a flowchart 98 for preparing or forming a graft is shown. Reference is made to the station 20 of FIGS. 1-2 and 4-5 for illustrative purposes. The method 98 can be utilized to dimension or shape a graft, such as a bone graft for repairing a bone defect. Fewer or additional steps than are recited below could be performed within the scope of this disclosure, and the recited order of steps is not intended to limit this disclosure.

A graft G can be harvested at step 98A (shown in dashed lines for illustrative purposes). The graft G can be autologous bone harvested from the humerus, for example. One would understand how to harvest bone tissue in view of the teachings disclosed herein. An inner bore GB can be defined in the graft G for receiving an anchoring member (GB shown in dashed lines for illustrative purposes). The anchoring member can be an elongated peg or screw, for example.

At step 98B, the graft G is secured to a raise plate 84. Step 98B can including selecting a graft tray or raise plate 84 from a set of graft trays or raise plates 84 based on a geometry of the bone graft G (see, e.g., raise plates 84-1, 84-2 of FIG. 12). One of the raise plates 84 can be selected with respect to a corresponding graft diameter of the bone graft G (e.g., 25 mm or 30 mm, as illustrated in FIG. 12).

The graft G is moved in a direction D2 (FIG. 2) and brought into abutment with the raise plate 84 (see FIGS. 4-5). The graft G can be wedged or pressed securely in the graft cavity 97 of the raise plate 84 (see FIG. 15).

At step 98C, the raise plate 84 is moved in a direction D3 (FIG. 2) and is assembled or otherwise secured to the cart assembly 24 (FIG. 3 with the graft G omitted, see also FIGS. 1 and 4-5). The raise plate 84 can be mounted to the cart assembly 24 such that the plate opening 83 extends along the drive axis DA (see FIG. 5). The raise plate 84 is secured to the cart assembly 24 such that the graft G is positioned between the tilt plate 68 and raise plate 84.

At step 98D, the clamp knob 80 is rotated in a direction R2 (FIG. 2) about the drive axis DA, causing the tilt plate 68 to move into abutment with the graft G to secure the graft G between the raise plate 84 and the tilt plate 68 (see FIGS. 1 and 4-5). The clamp knob 80 can be further rotated in the direction R2 to clamp or compress the graft G in the graft opening 97 between the flange portion 88 of the raise plate 84 and the proximal face 73 of the tilt plate 68.

At step 98E, the cart assembly 24 is secured to the base assembly 22. The cart assembly 24 is moved in a direction D3 (FIG. 2) along the drive axis DA relative to the base assembly 22, and the guide rails 70 are inserted into the guide channels 56 (guide rail 70 shown in dashed lines in FIG. 5 for illustrative purposes). The cart assembly 24 is translated or otherwise moved along the drive axis DA relative to the base assembly 22 such that the graft G is situated adjacent to the base guide 28 (see FIGS. 1 and 4-5).

A predefined maximum thickness of the resultant graft to be formed or shaped from the graft G is selected. The cart assembly 24 is advanced along the drive axis DA until a thickness indicator TI1 on the support body 26 is aligned with a ruler TI2 on the cart body 66 to match with or select the predefined maximum thickness, as illustrated by FIG. 1. The control knob 62 is rotated in a direction R3 (FIG. 4) to lock or otherwise secure the cart body 66 relative to the support body 26 at a position corresponding to the predefined maximum thickness.

At step 98F, the base guide 28 is oriented relative to the support body 26. A predefined graft angle of an edge face of the resultant graft is selected. The base guide 28 is swiveled or pivoted in a direction R4 (FIG. 5) about the rotational axis RA to adjust an angle of the reference plane REF relative to the drive axis DA (FIGS. 4-5). The base guide 28 is pivoted until an angle indicator AI1 on the support body 26 is aligned with an angular scale AI2 on the arm portion 38 (FIG. 1) to match with or select the predefined graft angle corresponding to a cutting angle of the cutting slot 32. The control knob 58 is rotated in a direction R5 (FIG. 4) to lock or otherwise secure the base guide 28 relative to the support body 26 at a position corresponding to the predefined graft angle, as illustrated in FIGS. 1 and 4.

Various techniques can be utilized to select the maximum thickness and graft angle parameters. For example, a defect in the glenoid can be characterized by the Walch Classification. The surgeon can measure bone loss utilizing imaging of the surgical site, such a radiogram or computed tomography technique, or can approximate a profile of the defect utilizing one or more sizers and/or measuring devices placed against the bone surface.

At step 98G, the graft G is dimensioned or shaped with respect to the desired or selected maximum thickness and graft angle of the resultant graft. For example, the graft G can be dimensioned or shaped such that the resultant graft has a generally tapered or wedge shaped geometry, as illustrated by graft portion GP between the reference plane REF and the arcuate flange 96 of raise plate 84 in FIG. 5 (see also graft G' of FIGS. 17-18). The instrument T is moved in a direction D4 (FIG. 2) to position or otherwise move the instrument T through the cutting slot 32. Thereafter, the graft G is dimensioned by cutting the graft G along the reference plane REF (see FIGS. 4-5). The reference plane REF intersects the graft G such that the graft G is cut through the cutting slot 32 at a position between the tilt plate 68 and raise plate 84 (see FIGS. 4-5).

At step 98H, the graft G including the resultant portion or graft G' (FIGS. 17-18) and remainder portion is removed from the station 20. Step 98H can include loosening the control knob 60 and moving the cart assembly 24 in a direction away from base guide 28 until the cart assembly 24 is disassembled from the base assembly 22. The clamp knob 80 is loosened to move the tilt plate 68 away from the graft G. Thereafter, the portions of the graft G are removed from the raise plate 84. The surgeon can insert a finger or instrument through the flange opening 83 to urge the cut portions of the graft G away from the support flange 82.

Figure 17:
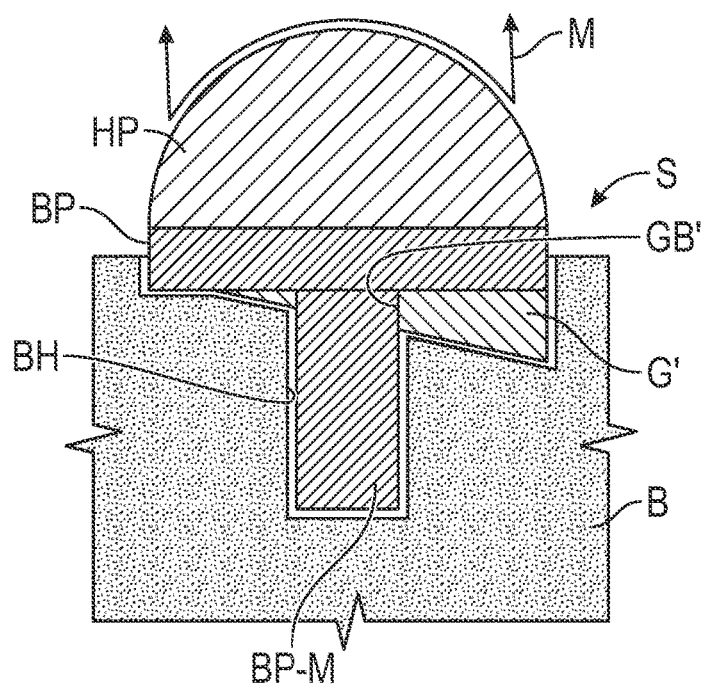
FIG. 17 schematically illustrates a graft positioned at a surgical site.
Figure 18:
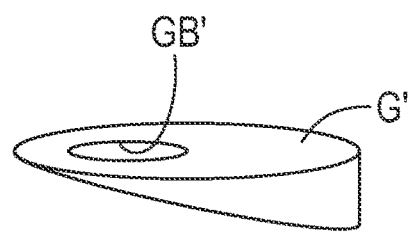
FIG. 18 illustrates an isolated perspective view of the resultant graft of FIG. 17.

Referring to FIG. 17, with continued reference to FIG. 16, a surgeon can position the shaped or resultant graft G' (see also FIG. 18) at a surgical site S at step 98I. In an embodiment, the surgical site S is a glenoid of a shoulder joint. However, the method could be performed to repair defects in various other bones within the scope of this disclosure. In other words, this disclosure is in no way limited to repairing bone defects of the glenoid.

Step 98I can include placing or otherwise securing the resultant graft G' to an implant such as a bone plate BP. The graft G' is oriented relative to the defect. The bone plate BP can include an anchoring member BP-M that is dimensioned to extend through an inner bore GB' of the resultant graft G' to secure the bone plate BP at the surgical site S. The graft G' is dimensioned to extend along a backside of the bone plate BP such that at least a portion of the graft G' is spaced apart from a sidewall of the bone plate BP, as illustrated in FIG. 17. The bone plate BP can be situated at surgical site S such that the backside of the bone plate BP abuts against surfaces of the bone hole BH.

The surgical site S may be prepared for receiving the graft G' and at least a portion of the bone plate BP. This may include forming at least one recess or hole BH in bone B at the surgical site S. The hole BH may be drilled, punched, tapped, or otherwise formed. The hole BH can be dimensioned to at least partially receive the bone plate BP and resultant graft G'. The hole BH may be formed to remove tissue from a defect in the bone B.

A head portion or glenosphere HP can be secured to the bone plate BP to provide an articulating surface for mating with an opposed articulating member M. The articulating member M can be an implant secured to the humerus, for example. In other embodiments, the bone plate BP provides the articulating surface.

The novel devices and methods of this disclosure provide versatility in dimensioning or shaping a graft. The graft can be shaped to more closely approximate a contour of a bone surface, such as a bone void, which can lead to improved healing at the surgical site.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A graft preparation station for dimensioning a bone graft comprising:
   a base assembly including a base guide secured to a support body to establish a passageway, the base guide defining a cutting slot extending along a reference plane between an outer face of a guide body of the base guide and a periphery of the passageway, and the reference plane intersecting a longitudinal axis of the passageway; and
   a cart assembly including a cart body and a mounting plate carried by the cart body; and
   wherein the base guide is pivotable about a rotational axis to adjust an angle of the reference plane relative to the longitudinal axis, and the rotational axis is established at a position along the reference plane between the outer face of the guide body and a bone graft mountable to the mounting plate.

2. The graft preparation station as recited in claim 1, wherein the rotational axis intersects the cutting slot.

3. The graft preparation station as recited in claim 1, wherein the rotational axis is spaced apart from the support body.

4. The graft preparation station as recited in claim 1, wherein the guide body spans between first and second arm portions to establish an archway over the bone graft, and the first and second arm portions are coupled to the support body.

5. The graft preparation station as recited in claim 4, wherein the guide body includes a beam interconnecting a first strut and a second strut to establish the archway, the outer face extends along the beam, the first and second struts are arranged on opposite sides of the passageway, and the first and second struts extend from the respective first and second arm portions.

6. The graft preparation station as recited in claim 5, wherein the cutting slot extends through the first and second struts such that opposed portions of the cutting slot are aligned with the bone graft along the reference plane.

7. The graft preparation station as recited in claim 4, wherein the first and second arm portions are moveable along an arc path relative to the support body to adjust the angle of the reference plane, and the arc path is established by a radius swept about the rotational axis.

8. The graft preparation station as recited in claim 1, wherein the cart body and the support body are moveable relative to each other to adjust a distance between the reference plane and the mounting plate.

9. The graft preparation station as recited in claim 8, wherein the cart body is moveable along the longitudinal axis of the passageway to adjust the distance between the reference plane and the mounting plate.

10. The graft preparation station as recited in claim 1, further comprising:
    at least one raise plate releasably secured to the cart body; and
    wherein the at least one raise plate and the mounting plate are movable relative to each other to compress the bone graft.

11. The graft preparation station as recited in claim 10, wherein:
    the at least one raise plate includes a base portion and a flange portion extending outwardly from the base portion, the flange portion is opposed to the mounting plate in an installed position, and the base portion is dimensioned such that the bone graft sits on the base portion; and
    the at least one raise plate is a plurality of raise plates, and the base portion of each of the raise plates is dimensioned to elevate the bone graft at different respective heights relative to the cart body.

12. The graft preparation station as recited in claim 11, wherein the rotational axis is established between the outer face of the guide body and the base portion of the respective raise plate secured to the cart body.

13. A graft preparation station for dimensioning a bone graft comprising:
    a base assembly including a base guide secured to a support body, the base guide defining a cutting slot extending along a reference plane intersecting a passageway through the base guide, wherein the base guide is pivotable about a rotational axis defined along the reference plane, and the rotational axis intersects the cutting slot; and
    a cart assembly including a cart body and a mounting plate carried by the cart body, the mounting plate dimensioned to mount a bone graft in the passageway at a position along the reference plane.

14. The graft preparation station as recited in claim 13, wherein the rotational axis is spaced apart from the support body.

15. The graft preparation station as recited in claim 13, wherein the base guide includes first and second struts on opposite sides of the passageway, the cutting slot extends through the first and second struts such that opposed portions of the cutting slot are aligned with the bone graft along the reference plane.

16. The graft preparation station as recited in claim 15, wherein the base guide includes a beam spanning between the first and second struts to establish an archway over the bone graft, the cutting slot extends through the beam, and the rotational axis is spaced apart from the beam.

17. The graft preparation station as recited in claim 16, wherein the base guide includes first and second arm portions coupling the first and second struts to the support body, the first and second arm portions are moveable along an arc path to adjust an angle of the reference plane relative to a longitudinal axis of the passageway, and the arc path is established by a radius swept about the rotational axis.

18. The graft preparation station as recited in claim 13, wherein the cart body and the support body are moveable relative to each other to adjust a distance between the reference plane and the mounting plate.

19. The graft preparation station as recited in claim 18, wherein the cart body is moveable through the passageway to adjust the distance.

20. The graft preparation station as recited in claim 13, further comprising:
    a graft tray releasably secured to the cart body; and
    wherein the graft tray and the mounting plate are movable relative to each other to compress the bone graft at the position along the reference plane.

* * * * *